United States Patent [19]

Grundei et al.

[11] Patent Number: 5,480,451
[45] Date of Patent: Jan. 2, 1996

[54] ANGULARLY ADJUSTABLE OFFSET SPHERICAL HEAD ENDOPROSTHESIS

[75] Inventors: Hans Grundei, Lübeck; Heinz Moser, Oestrich-Winkel, both of Germany

[73] Assignee: Eska Medical GmbH & Co., Lubeck, Germany

[21] Appl. No.: 106,152

[22] Filed: Aug. 12, 1993

[30] Foreign Application Priority Data

Aug. 17, 1992 [DE] Germany .......................... 42 27 139.8

[51] Int. Cl.$^6$ .................. A61F 2/36; A61F 2/32
[52] U.S. Cl. .................. 623/23; 623/18; 623/22
[58] Field of Search .................. 623/18, 19, 22, 623/23

[56] References Cited

U.S. PATENT DOCUMENTS

| | | | |
|---|---|---|---|
| 3,685,058 | 8/1972 | Tronzo | 128/92 |
| 4,312,079 | 1/1982 | Dörre et al. | 623/23 X |
| 5,002,581 | 3/1991 | Paxson et al. | 623/23 |
| 5,314,479 | 5/1994 | Rockwood, Jr. et al. | 623/19 |

FOREIGN PATENT DOCUMENTS

| | | |
|---|---|---|
| 2574283 | 6/1986 | France . |
| 0363019 | 4/1990 | Germany . |

*Primary Examiner*—David Isabella
*Assistant Examiner*—Laura Fossum
*Attorney, Agent, or Firm*—Panitch Schwarze Jacobs & Nadel

[57] ABSTRACT

A spherical head endoprosthesis has a spherical head and a base piece. Between the base piece and the spherical head is a conical interference fit connection, wherein the spherical head has a conical bore and the base piece has a conical pin. The axis of the conical bore and the center line of the spherical head form an angle in the range of 7° to 15°. The conical bore is decentralized in relation to the center line with an offset of 1 to 4 mm. On the inside of the bore are at least five grooves parallel to the axis of the bore, into which, after assembly of the conical interference fit connection, grips at least one locking projection provided on the peripheral surface of the conical pin. The grooves may be designated by markings around the periphery of the bore opening for easy identification of the proper groove for insertion of the locking projection during the replacement operation.

12 Claims, 2 Drawing Sheets

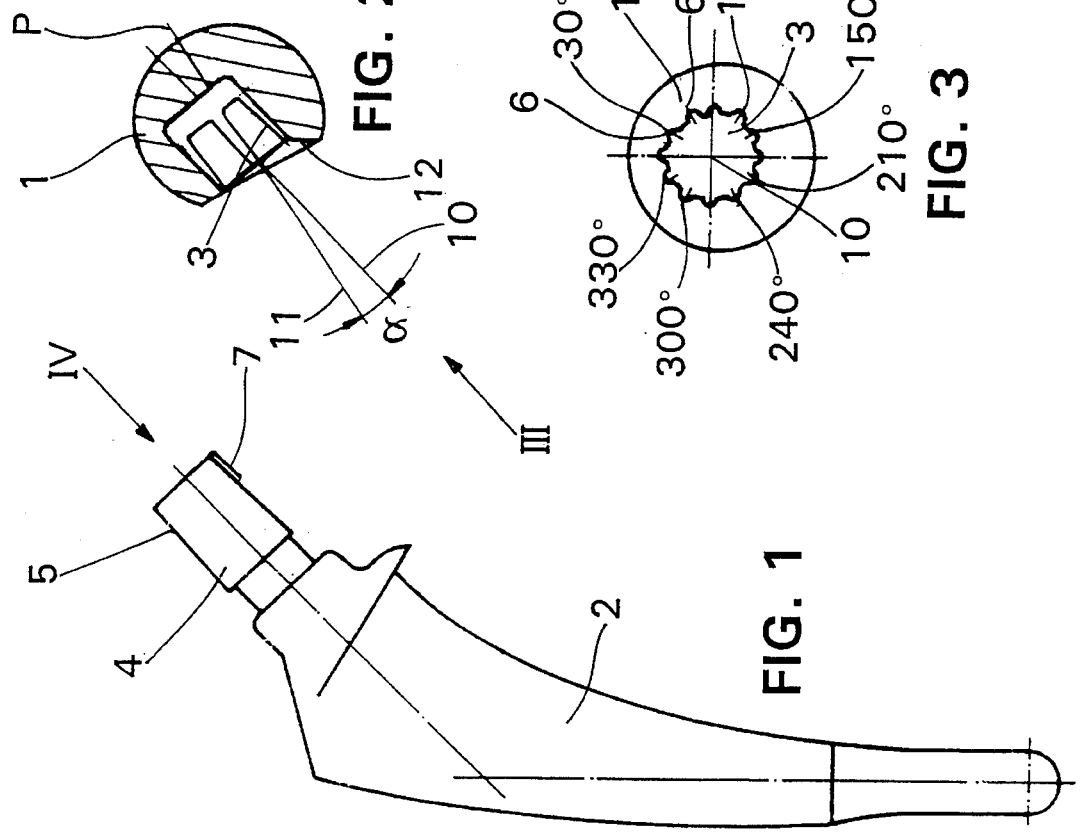

ANGULARLY ADJUSTABLE OFFSET SPHERICAL HEAD ENDOPROSTHESIS

FIELD OF THE INVENTION

The present invention relates to a spherical joint endoprosthesis which simulates a natural ball joint and is connected by means of a conical interference fit connection to a base piece which can be anchored in a bone, wherein the base piece has a conical pin and the spherical head has a conical bore.

BACKGROUND OF THE INVENTION

Such spherical joint endoprostheses have been known for a long time and have proven themselves in surgical procedures. Unfortunately there are a number of problems associated with the known endoprostheses. For example, during implantation of a femur shaft component of a total hip joint endoprosthesis after the insertion of the shaft into the modular area of the femur bone, it is difficult to achieve the exact orientation of the shaft piece in such a manner that the artificial joint ball to be connected with the femur shaft component shows no luxation tendencies after the implant. This is caused by the shaft piece and the conical pin being arranged at a fixed angle to each other for the assembly of the conical interference fit connection between the shaft piece and the spherical head.

An adjustment to the individual needs of the patient is very difficult, since even with the most modern x-ray technology, these needs are usually first recognized during surgery, and the surgeon cannot simply try various endoprostheses until the right one is determined from a supply. An adjustment to the individual patient's needs includes the already mentioned reduction of the luxation tendency, occasionally a lengthening of the leg, a force equalization of the muscular antagonists in all four directions (medially, laterally, dorsally, ventrally), or the compensation for a valgus or varus formation of the thigh neck of the leg in question.

Examples of prior art devices which attempt to solve the above difficulties with varying degrees of success are shown, for example, in European published patent application 0 363 019 A2 and German Gebrauchsmuster 91 03 574 U1 and 89 01 018 U1.

A further major problem arises that the surgeon before the intervention in the course of planning the operation with the help of surgical models, tries to shape the endoprosthesis optimally in advance, so that during the operation he is not further burdened with determining the optimal position of the spherical head on the base piece. Without additional means the surgeon on the following day, that is the day of the operation, stands in the operating room with the known joint endoprosthesis in exactly the same situation as during the operation planning, since no aids are available to him to again find the position of the ball joint on the base piece which was determined the day before to be optimal.

Given this background, it is the object of the present invention to further develop a spherical joint endoprosthesis of the above-described type, so that it enables the surgeon even during the surgery to make fine adjustments of the spherical head in relation to the base piece according to the individual needs of the patient, and further enables the surgeon to easily find during the operation (i.e., in situ) the optimal position of the spherical head on the base piece, which was previously determined during the planning of the operation.

SUMMARY OF THE INVENTION

This object is achieved according to the present invention by a spherical head endoprosthesis having a spherical head simulating the natural joint ball, connectable by means of a conical interference fit connection with the base piece to be anchored in the bone, wherein the base piece comprises a conical pin and the spherical head comprises a conical bore, and wherein the conical bore is built into the spherical head offset from the longitudinal axis of the spherical head (i.e., decentralized or eccentric) and angularly tilted with respect to this longitudinal axis. Further, the conical bore in the spherical head is provided with grooves parallel to its longitudinal axis, and the conical pin which is interference fit into the conical bore has a locking projection which grips into one of the grooves to prevent rotation of the spherical head after assembly and implantation.

According to the invention the axis of the conical bore and the center line of the spherical head, which extends through the pole and the geometrical center point of the spherical head, form an angle in the range of 7° to 15°. Therefore, the conical bore in this angle range is, so to speak, obliquely built into the spherical head. Furthermore, the bore is decentrally arranged in the spherical head at an offset of 1 to 4 mm from the center line. That is, to the angled offset of 7° to 15° is added a translateral offset of 1 to 4 mm.

If this spherical head is placed on the conical pin and rotated, then it is apparent that the geometric middle point of the spherical head will be rotated at an offset distance of 1 to 4 mm (depending on the amount of the offset) around the longitudinal axis of the conical pin. Simultaneously, the pole of the spherical head will describe a locus curve in the shape of a circle. Thereby the longitudinal axis of the conical pin and the center line through the pole and the geometric middle point of the spherical head form an angle of between ±7° and ±15°, depending on at what angle the conical bore has been built into the spherical head, the reference line being the longitudinal axis of the conical pin.

From the foregoing it is clear what degree of freedom the surgeon has during surgery in finding for each patient the optimal position of the spherical head in relationship to the base piece. This construction allows the already discussed adjustment to be carried out effortlessly in situ, especially to compensate for a valgus— or varus formation, for example, of the leg concerned, to change the length of the leg, or to equalize the tension of the muscular antagonists medially to laterally and dorsally to ventrally.

By means of the following feature the degree of freedom of the adjustment will be reduced, but the safety against an unintentional changing of the optimally found position is considerably increased. Inside the conical bore there are provided at least five grooves parallel to the axis of the bore, into which grips, after assembly of the conical interference fit connection, at least one locking projection on the peripheral surface of the conical pin. The at least five grooves parallel to the axis are equidistantly distributed around the inside the bore. In the case of five grooves, the grooves are angularly spaced at an angle of 72° from each other.

The surgeon can therefore plan the operation before the intervention and determine the optimal position of the spherical head in relation to the base piece. Above all, he can easily note the position, and find it again without problem on the day of the operation. In the case of five grooves he need only note whether the angle 72°, 144°, etc. is to be used. By the placement of markings this can be still further simplified.

Preferably, the stated locking projection is arranged at the proximal end of the conical pin, that is on the end facing the spherical head, and indeed in the medial direction. This considerably increases the security against fracture of the locking projection and thereby the stability of the selected spherical head position in reference to the base piece. Thereby, the locking projection is arranged on the side of the conical pin which is the least loaded. In the same manner, the locking into one of the grooves inside the conical bore of the spherical head is also guaranteed with different sized spherical heads. Therefore, the surgeon can be provided with a sort of kit of standardized endoprosthesis pieces, consisting of standardized base pieces and standardized spherical heads, for example, of different sizes and with differently angled offsets of the conical bore in the spherical head and/or with different eccentricities of the conical bore in the spherical head, so that the surgeon during the surgery can optimally assemble an appropriate spherical joint endoprosthesis.

According to an especially preferred embodiment, the inside of the conical bore comprises twelve grooves parallel to the axis and equidistantly spaced from each other at an angular distance of 30°. This guarantees a generally sufficient variability.

The material preferred for use as a spherical head is a biologically compatible metal or a bioceramic, which has sufficient hardness.

Especially preferred is the usage of the previously described spherical head endoprosthesis as a ball joint component of a total hip joint endoprosthesis, according to which the base piece comprises a femur shaft component and the pelvic socket comprises an artificial hip joint socket, as well as a ball joint component of a total shoulder joint endoprosthesis, according to which the base piece comprises a humerus shaft component and a joint socket cap of an artificial shoulder joint socket cap. As the gliding partner for the spherical head, an inlay of high density polyethylene, polyurethane and/or ceramic is especially preferred.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is a side view of a base piece, here a femur shaft component;

FIG. 2 is a cross-sectional view of the spherical head;

FIG. 3 is a view of the spherical head of FIG. 2 in the direction of the arrow III;

FIG. 4 is a view of the conical pin of the base piece of FIG. 1 in the direction of the arrow IV;

In the drawings, like numerals are used to indicate like elements throughout.

DETAILED DESCRIPTION OF PREFERRED EMBODIMENTS

Figure 6:
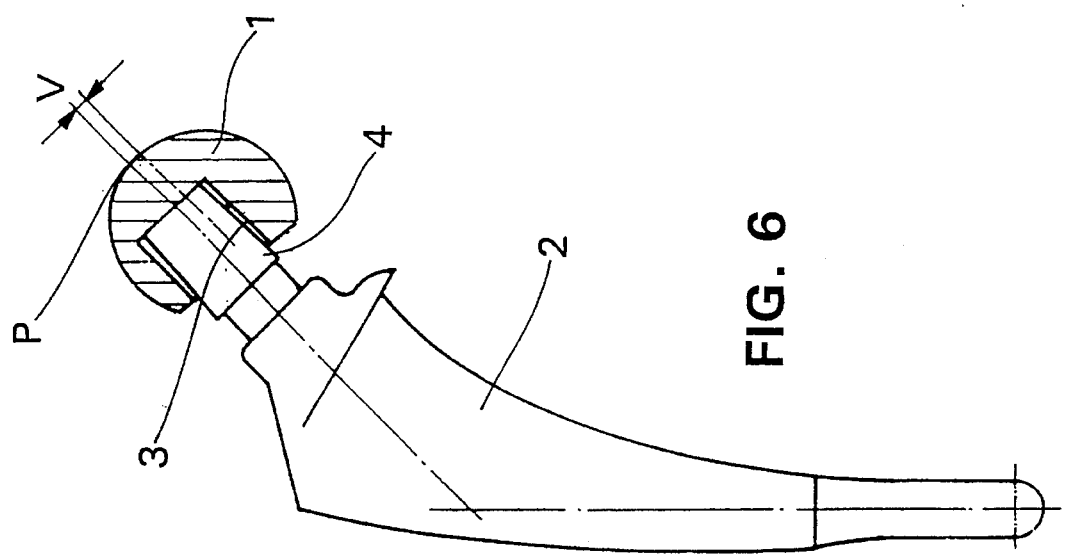
FIG. 6 is a corresponding side view as in FIG. 5, but in a varus position.

In FIG. 1 a base piece 2 is displayed, here in the form of a femur shaft component. At its joint-facing end a conical pin 4 is formed for providing a conical interference fit connection with the spherical head 1. On the peripheral surface 5 of the conical pin 4, a locking projection 7 is provided at the proximal end of the conical pin 4. This points in a medial direction. This has the advantage that the locking projection, under load of the implant, lies on the side with the least load.

In FIG. 2 a cross-sectional view of the spherical head 1 of the spherical head endoprostheses is shown. Inside the spherical head is a conical bore 3, which is so dimensioned that the spherical head 1 sits on the base piece 2 by means of a conical interference fit connection between the conical bore 3 and the conical pin 4.

As seen in FIG. 2, the axis 10 of the conical bore 3 and the center line 11, which extends through the pole P of the spherical head 1 as well as through its geometric center point, form an angle $\alpha$ which lies in the range of 7° to 15°. By the tilted position of the bore axis 10 a chamfer 12 is created in an area of the bore edge.

Figure 5:
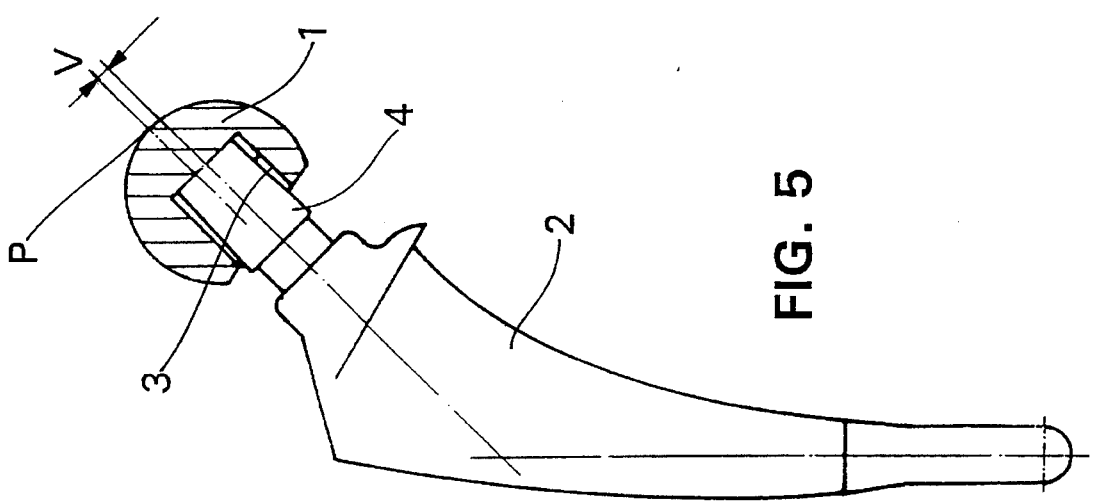
FIG. 5 is a side view, partially in cross section, of the assembled spherical head endoprosthesis in a valgus position.

The bore 3 is not only bored at a tilt in the spherical head 1, it is decentralized from the center line 11 by an offset V (see FIGS. 5 and 6). The offset V can be 1 to 4 mm.

FIG. 3 shows the view of the spherical head 1 in the direction of the arrow III in FIG. 2. Again, the translateral offset is clearly visible, that is, the decentralizing of the bore 3 in the spherical head 1.

On the inner periphery of the bore 3 in the displayed embodiment twelve grooves 6 are arranged running parallel to the axis 10. After assembly of the conical interference fit connection between the conical bore 3 and the conical pin 4, the locking projection 7 grips into one of the grooves 6 and forms a rotational block against an unintentional turning during load on the endoprosthesis.

As shown in FIG. 3, the face of the spherical head 1 around the periphery of the opening to the bore 3 may be provided with suitable markings, such as degree notations 30, 60, 120, 150, etc., adjacent to one or more of the grooves 6 to designate the different grooves. Such markings allow the surgeon to easily find during the operation the appropriate groove for insertion of the locking projection 7, so that the spherical head will have the proper position when assembled with the base piece 2 according to the operation plan. It will be understood, of course, that other markings besides degree notations, or other marking locations could be used.

FIG. 4 is an enlarged view of the pin 4 in the direction of the arrow IV in FIG. 1. The locking projection 7 is clearly visible sitting on the peripheral surface 5 of the pin 4.

In FIGS. 5 and 6 the assembled spherical head endoprosthesis is displayed in the form of the femur component of a total-joint endoprosthesis. In FIG. 5 the spherical head is rotated into such a position which is used, for example, to compensate for a valgus formation of the leg. The other extreme in this plane is shown in FIG. 6, in which the spherical head 1 is rotated 180° in comparison to the position in FIG. 5. This position is ideal to compensate for a varus formation of the leg.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A spherical head endoprosthesis comprising a spherical head simulating a natural joint ball connectable by means of a conical interference fit connection with a base piece to be anchored in a bone, wherein the base piece comprises a conical pin and the spherical head comprises an exterior surface and a conical bore having an opening, a longitudinal axis (10) and a center line (11), the longitudinal axis (10) of the conical bore (3) and the center line (11) of the spherical head defining an angle α of about 7° to 15°, the conical bore (3) in the spherical head being offset in an amount of about 1–4 mm relative to the center line (11), the bore (3) being provided with at least five grooves (6) parallel to the longitudinal axis (10) of the bore, and a single locking projection (7) on a peripheral surface (5) of the conical pin (4), said projection gripping into one of said at least five grooves (6) after assembly of the conical interference fit connection, and markings provided adjacent to said bore (3) on the spherical head to identify at least the one of said at least five grooves (6) into which said projection is to be inserted prior to assembly of the conical interference fit connection.

2. A spherical head endoprosthesis according to claim 1 wherein the locking projection (7) is provided at a proximal end of the conical pin (4) and projects in a medial direction.

3. A spherical head endoprosthesis according to claim 1 where the inside surface of the conical bore is provided with twelve grooves (6) parallel to the longitudinal axis of the bore and equidistantly spaced.

4. A spherical head endoprosthesis according to claim 2 where the inside surface of the conical bore is provided with twelve grooves (6) parallel to the longitudinal axis of the bore and equidistantly spaced.

5. A spherical head endoprosthesis according to claim 1 wherein the spherical head (1) is made of metal.

6. A spherical head endoprosthesis according to claim 2 wherein the spherical head (1) is made of metal.

7. A spherical head endoprosthesis according to claim 3 wherein the spherical head (1) is made of metal.

8. A spherical head endoprosthesis according to claim 1 wherein the spherical head (1) is made of ceramic.

9. A spherical head endoprosthesis according to claim 2 wherein the spherical head (1) is made of ceramic.

10. A spherical head endoprosthesis according to claim 3 wherein the spherical head (1) is made of ceramic.

11. A spherical head endoprosthesis according to claim 1 wherein said markings are provided adjacent to each of said at least five grooves.

12. A spherical head endoprosthesis according to claim 11 wherein said markings correspond to angular positions of the grooves (6) around the periphery of the opening to the bore (3).

* * * * *